United States Patent
Bohn et al.

(10) Patent No.: US 8,143,597 B1
(45) Date of Patent: Mar. 27, 2012

(54) REMOTE SENSING PHASE FLUORIMETRY USING MERCURY VAPOR LAMP

(75) Inventors: Matthew J. Bohn, Beavercreek, OH (US); Michael A. Lundin, Burke, VA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 562 days.

(21) Appl. No.: 12/353,015

(22) Filed: Jan. 13, 2009

Related U.S. Application Data

(60) Provisional application No. 61/063,875, filed on Jan. 14, 2008.

(51) Int. Cl.
*G01J 1/58* (2006.01)
*G01T 1/10* (2006.01)
(52) U.S. Cl. ............... 250/458.1; 250/459.1; 250/462.1
(58) Field of Classification Search .... 250/458.1–461.2, 250/483.1
See application file for complete search history.

(56) References Cited

U.S. PATENT DOCUMENTS

| | | | | |
|---|---|---|---|---|
| 4,336,459 A * | 6/1982 | Fay | ............................ | 250/459.1 |
| 5,792,663 A * | 8/1998 | Fry et al. | .......................... | 436/73 |
| 5,863,460 A * | 1/1999 | Slovacek et al. | ......... | 252/301.35 |
| 5,909,278 A * | 6/1999 | Deka et al. | ..................... | 356/318 |
| 6,426,505 B1 * | 7/2002 | Rao et al. | .................... | 250/458.1 |
| 2004/0090622 A1 * | 5/2004 | Nielsen et al. | ................ | 356/317 |
| 2004/0239916 A1 * | 12/2004 | Seino et al. | .................. | 356/28.5 |

* cited by examiner

*Primary Examiner* — David Porta
*Assistant Examiner* — Casey Bryant
(74) *Attorney, Agent, or Firm* — AFMCLO/JAZ

(57) ABSTRACT

An efficient and portable method for remote detection of a target mineral material through frequency domain fluorimetry, a detection technique that measures the time lag between absorption and emission of photons, thereby determining the lifetime of said target mineral material. As claimed and disclosed in the present invention, mercury vapor lamps, a common source of industrial facility lighting, emit radiation that overlaps the UV/blue absorption spectrum of many fluorophores and may be used as an efficient and portable excitation source for remote frequency domain fluorimetry.

22 Claims, 4 Drawing Sheets

REMOTE SENSING PHASE FLUORIMETRY USING MERCURY VAPOR LAMP

The invention described herein may be manufactured and used by or for the Government of the United States for all governmental purposes without the payment of any royalty.

BACKGROUND OF THE INVENTION

The invention relates to phase fluorimetry or frequency domain fluorimetry.

Frequency Domain fluorimetry is a detection technique that measures the time lag between absorption and emission of photons thereby determining the lifetime of a fluorophore. A fluorophore is defined as a member of an atomic group with one excited molecule that emits photons and is fluorescent. The excitation modulation will result in an emission delay relative to excitation, and can be measured as a phase shift. The lifetime is determined by measuring the phase shift and amplitude of the fluorescence when an excitation source is sinusoidally modulated.

Frequency Domain (FD) Fluorimetry, capitalizes on the frequency response function of a fluorophore and offers independence from light scatter and excitation/emission intensity variations in order to extract a sample's fluorescent lifetime. Light scatter can be a significant problem in pulsed excitation measurements because the intense laser pulse can overwhelm the weak fluorescent signal. This problem is alleviated in continuous wave (CW) frequency domain fluorimetry measurements because the excitation source is not as intense. In addition, since the method ratios the fluorescence to the excitation intensity as a function of modulation frequency, any variations in excitation intensity will be automatically removed from the data. Samples which fluoresce in the visible range are commonly excited with ultraviolet laser sources, which can be problematic because they are not typically high power, portable devices.

The simplest model for the temporal response of a fluorophore is a single exponential decay. By abruptly terminating the excitation source (for example, a pulsed ultraviolet laser) and then observing the fluorescent intensity as a function of time, the decay can be observed, averaged and stored on a digitizing oscilloscope. The fluorescent lifetime, $\tau$, can be measured by fitting the decaying amplitude to an exponential decay:

$$I(t) = A_0 \exp\left(-\frac{t}{\tau}\right) \quad \text{Eq (1)}$$

An operator must ensure that the excitation source turns off much more quickly than $\tau$ and that the measurement equipment is much faster than $\tau$. Of course the lifetime of the fluorophore will depend on the properties of the host medium due to nonradiative relaxation mechanisms. The single exponential decay modeled above is actually an ensemble average of many fluorophores in the sample (i.e., there is actually a range of lifetimes observed in the sample, but we will assume that these can be averaged into a single decay lifetime). It is assumed in this research effort that the multi-exponential decay times are separated by less than 20 percent such that a single exponential decay is a valid mean value for the fluorophore.

Frequency Domain fluorimetry is a technique that determines the lifetime of a fluorophore by measuring the phase shift and amplitude of the fluorescence when the excitation source is sinusoidally modulated. The excitation modulation will result in an emission delay relative to excitation and can be measured as a phase shift. A sinusoidal excitation source with modulation frequency, $\omega$, will result in a frequency dependent fluorescence of:

$$I(t) \propto m(\omega)\sin(\omega t + \phi(\omega)), \quad \text{Eq (2)}$$

where the phase delay, $\phi(\omega)$, and modulation depth, $m(\omega)$, are determined by the lifetime of the fluorophore and the frequency by:

$$\tan(\phi(\omega)) = \omega\tau \text{ and } m(\omega) = \frac{1}{\sqrt{(1+\omega^2\tau^2)}}. \quad \text{Eq (3)}$$

In traditional Frequency Domain fluorimetry, the modulation frequency is varied and the phase and modulation amplitude are measured. Alternatively, the in-phase and quadrature components can be recorded and the lifetime calculation is extracted by least squares analysis of recorded data using the in-phase, $N_\omega$, and quadrature, $D_\omega$, amplitudes of the fluorescent intensity by:

$$N_\omega = \frac{\int_0^\infty I(t)\sin(\omega t)\,dt}{\int_0^\infty I(t)\,dt} \text{ and } D_\omega = \frac{\int_0^\infty I(t)\cos(\omega t)\,dt}{\int_0^\infty I(t)\,dt}, \quad \text{Eq (4)}$$

where the experimental values of $\phi_c(\omega)$ and $m_c(\omega)$ are given by $$\tan(\phi_c) = \frac{N_\omega}{D_\omega} \text{ and } m_c = (N_\omega^2 + D_\omega^2)^{1/2}. \quad \text{Eq (5)}$$

The lifetime can then be calculated such that $\chi^2$ is minimized in $$\chi^2 = \frac{1}{\nu}\sum_\omega \left(\frac{\phi-\phi_c}{\delta\phi}\right)^2 + \frac{1}{\nu}\sum_\omega \left(\frac{m-m_c}{\delta m}\right)^2, \quad \text{Eq (6)}$$

where the values of $\delta\phi$ and $\delta m$ represent the uncertainty in the measured values, and $\nu$ is the number of degrees of freedom.

As claimed and disclosed in the present invention, mercury vapor lamps, a common source of industrial facility lighting, emit radiation that overlaps the UV/blue absorption spectrum of many fluorophores and may be used as an efficient and portable excitation source. The AC power modulation of mercury vapor lamps modulates the lamp's intensity at 120 Hz (in the United States) and higher harmonics. The present invention offers a means to remotely detect fluorophores such as uranium from distances exceeding a kilometer. The present invention provides an option to exploiting Frequency Domain fluorimetry remotely and overcomes problems in the art of using high power laser sources by using commonly available equipment, often available at the site in question.

SUMMARY OF THE INVENTION

An efficient and portable method for remote detection of a target material through frequency domain fluorimetry, a detection technique that measures the time lag between absorption and emission of photons, thereby determining the lifetime of said target material. As claimed and disclosed in the present invention, mercury vapor lamps, a common source of industrial facility lighting, emit radiation that overlaps the UV/blue absorption spectrum of many fluorophores and may be used as an efficient and portable excitation source for remote frequency domain fluorimetry.

It is therefore an object of the present invention to provide an efficient and portable method for remote detection of a target material through frequency domain fluorimetry.

It is another object of the invention to provide an efficient and portable method for remote detection of a target material through frequency domain fluorimetry, a detection technique that measures the time lag between absorption and emission of photons, thereby determining the lifetime of said target material.

It is another object of the invention to provide an efficient and portable method for remote detection of a target material through frequency domain fluorimetry using mercury vapor lamps, a common source of industrial facility lighting, as an efficient and excitation source.

These and other objects of the invention are achieved by the description, claims and accompanying drawings and by:

an efficient and portable method for remote detection of a target material through frequency domain fluorimetry comprising the steps of:

choosing a target material to detect and identify;

selecting a mercury vapor lamp in close proximity to said target material for use as a target material fluorophore excitation source;

sensing sinusoidal modulation of said mercury vapor lamp from said selecting step due to power line fluctuations;

detecting fluorescence from said target material through excitation from said mercury vapor lamp;

measuring said sinusoidal modulation amplitude and phase angle of said mercury vapor lamp from said sensing step and comparing the difference to said fluorescence from said target material amplitude and phase angle from said detecting step; and determining lifetime of said target material and corresponding identity of said target material.

DETAILED DESCRIPTION

Mercury vapor lamps, a common source of industrial facility lighting, emit radiation that overlaps the UV/blue absorption spectrum of many fluorophores and may be used as an efficient and portable excitation source for frequency domain fluorimetry. Ultraviolet laser induced fluorescence requires high power when used for remote sensing of material lifetimes. By contrast, mercury vapor lamps, which are readily available and independently powered at many industry sites, offer up to 500 W in the UV/Blue spectrum. The arrangement of the present invention demonstrates a remote detection system and method using a multi-modulation frequency excitation of a common mercury vapor lamp. The mercury vapor lamp is simultaneously modulated at many harmonics of the supplied 50/60 Hertz power line, which enables multi-modulation frequency excitation. Although this technique is not as precise as conventional laser techniques, it offers a means to remotely detect fluorosphores such as uranium from distances exceeding a kilometer. This disclosed invention also has additional broader application in active remote sensing, such as chemical/biological agent detection through the use of tagants, which act as the fluorophore identifying the chemical/biological agent.

Figure 1:
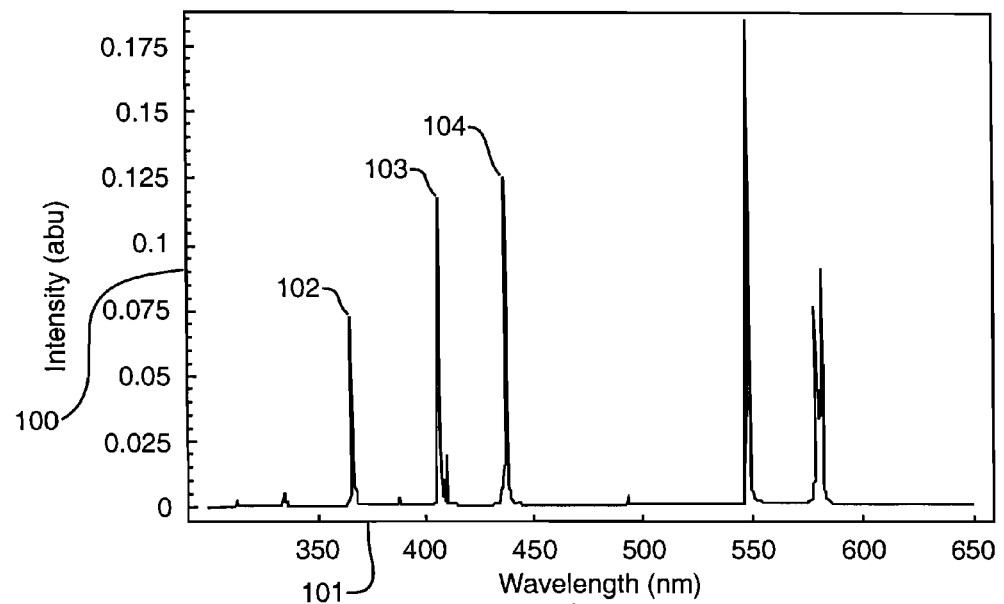
FIG. 1 is a mercury vapor lamp emission spectrum taken with a monochromator.

FIG. 1 shows a mercury vapor lamp emission spectrum taken with a monochromator. The y-axis 100 in FIG. 1 represents intensity and the x-axis 101 wavelength. Clear, or uncoated mercury vapor lamps emit approximately 50% of their optical output in the ultraviolet/blue region of the spectrum at 365 nm (shown at 102 in FIG. 1), 405 nm at 103 in FIG. 1, and 436 nm at 104 in FIG. 1.

Figure 2:
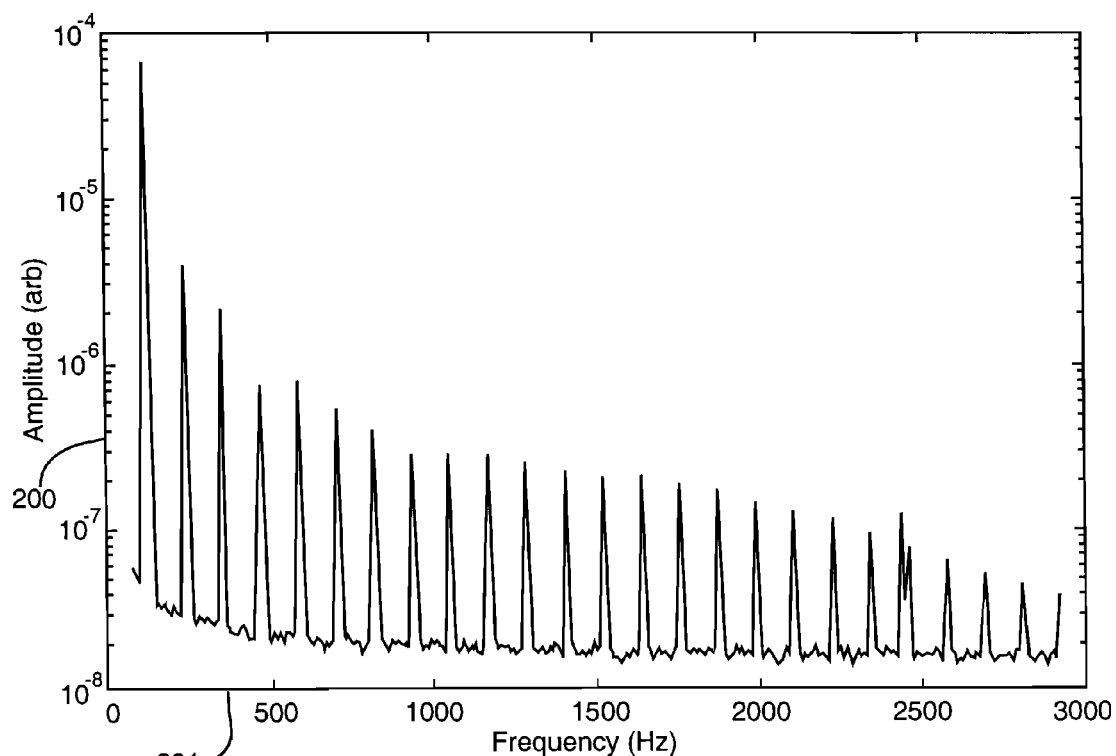
FIG. 2 is a mercury vapor lamp frequency modulation spectrum.

A significant aspect of the present invention is the capability to remotely detect uranium processing in hostile territories with suspected nuclear activities. In the present invention, minerals that contain $UO_2^{2+}$ were identified as suitable samples to test this significant aspect of the present invention, the absorption spectrum of $UO_2^{2+}$ ranging from 390-450 nm. All $UO_2$ containing rocks, minerals and glasses exhibit similar absorption peaks and high quantum yields, in the range of 40-80%, and long lifetime, ranging from 85-600 microseconds. Additionally, the fluorescence occurs at wavelengths in which the mercury vapor lamp has little output. Excitation modulation of the uranyl sources occurs from the mercury lamp, which is modulated at facility power frequencies and higher harmonics. FIG. 2 shows a fast Fourier transform of a 175 W clear mercury vapor lamp intensity. In FIG. 2, the y-axis 200 represents relative intensity and the x-axis 201 represents frequency. The integration time, or time of valid observation, will be roughly limited by the inverse of the facility power line width, and which standard value known in the art is ±0.05 Hz. FIG. 2 demonstrates that the mercury vapor lamp is modulated at 120 Hz and many higher harmonics. It is these higher harmonics that enable the frequency domain fluorimetry technique.

Figure 3:
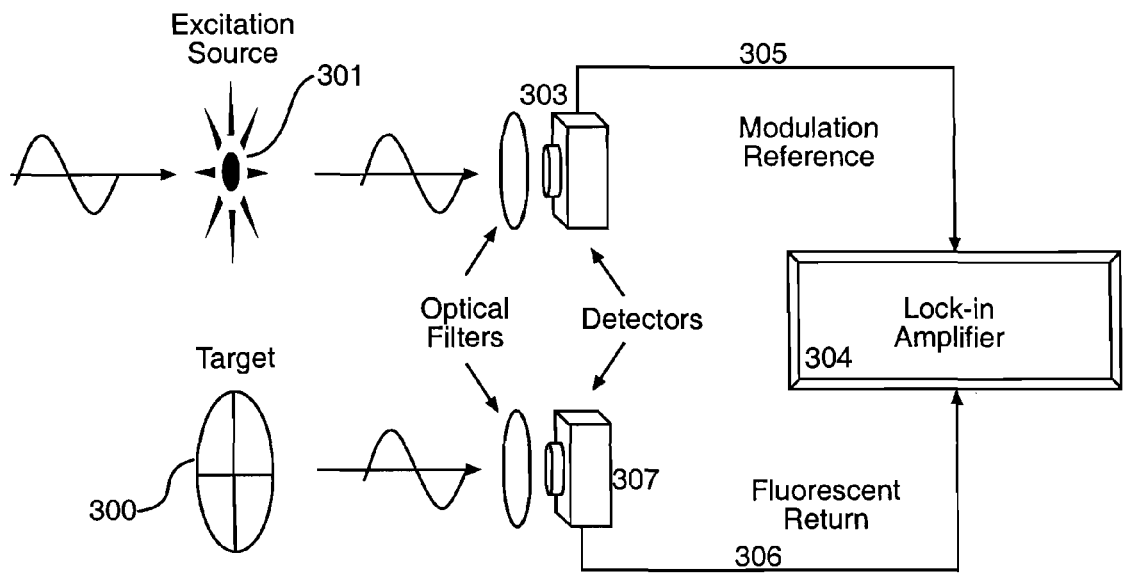
FIG. 3 is a preferred arrangement of the invention.

FIG. 3 shows a preferred arrangement of the invention. A target is shown at 300 and an excitation source is shown at 301. By way of example, the target 300 is a suspected uranium processing facility in hostile territory and the excitation source 301 is a mercury vapor lamp in the parking lot or affixed to the building of said facility. Two silicon detectors are shown at 303 and 307 and serve as an excitation reference detector at 303 and a sample fluorescence detector at 307. The information obtained through silicon detectors 303 and 307 are both filtered through optical filters, both illustrated at 302. The lock-in amplifier at 304 measures the modulation amplitude and the phase angle difference of the reference, illustrated at 305 to the fluorescence, illustrated at 306. Curve fitting is then performed to calculate the lifetime of the material.

Known hazards are associated with radiation source containment, so a sample of $UO_2^{2+}$ doped glass, commonly called Vaseline glass, which can be found in antique stores and typically contains less than 2% uranium, was used as a suitable surrogate to prove the concept in the preferred arrangement of the invention of FIG. 3. Authentication of Vaseline glass is performed by simply observing the glass under a common UV lamp to observe the bright green fluorescence, a common technique used by glass collectors. FIG.

Figure 4:
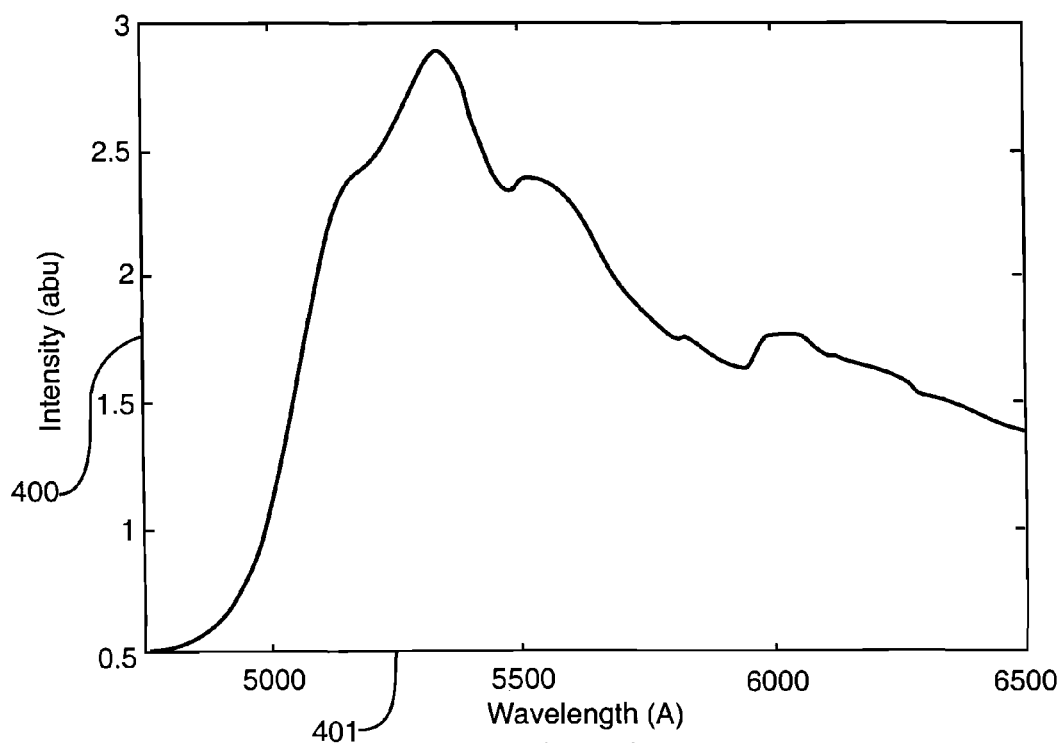
FIG. 4 is a graph of a steady state Vaseline glass emission.

4 shows a steady state spectrum using a silicon detector under excitation by a 1 W 425 LED and the envelope of the characteristic $UO_2^{2+}$ spectrum. The x-axis 401 represents wavelength and the y-axis 400 represents intensity. The FIG. 4 spectrum resulted from an LED excitation square wave modulated at 250 Hz, which allowed for nearly complete recovery in the glass sample. The lifetime was calculated from the decay curve data using Equation 1 and yielded $\tau$=268 μs.

In a preferred arrangement of the invention, a mercury vapor lamp was used as an excitation source, illustrated at 301 in FIG. 3, and the two silicon detectors filtered, illustrated at 302 in FIG. 3, with the reference detector 303 observing the mercury lamp and the second filter 307 observing the fluorescence. The lock-in amplifier locked to the strongest modulation frequency, 120 Hz, as the primary reference and was manually stepped through the harmonics to record the modulation amplitude and fluorescence values. For the mercury vapor lamp excitation, the amplitude of the power harmonics needed to be measured as a reference, so the light was detected with a photodiode and the modulation spectrum recorded on a spectrum analyzer. The data set was started at 360 Hz so that all data points could be taken at the same gain settings. Since there is a continuum of green from the mercury lamp, the background may need to be corrected, however, background contribution was found to be negligible. This preferred arrangement of the invention using the Vaseline glass to detect for uranyl compounds yielded $\tau$=254 μs, which is in excellent agreement with the exponential decay calculation from using the LED as an excitation source.

Figure 5:
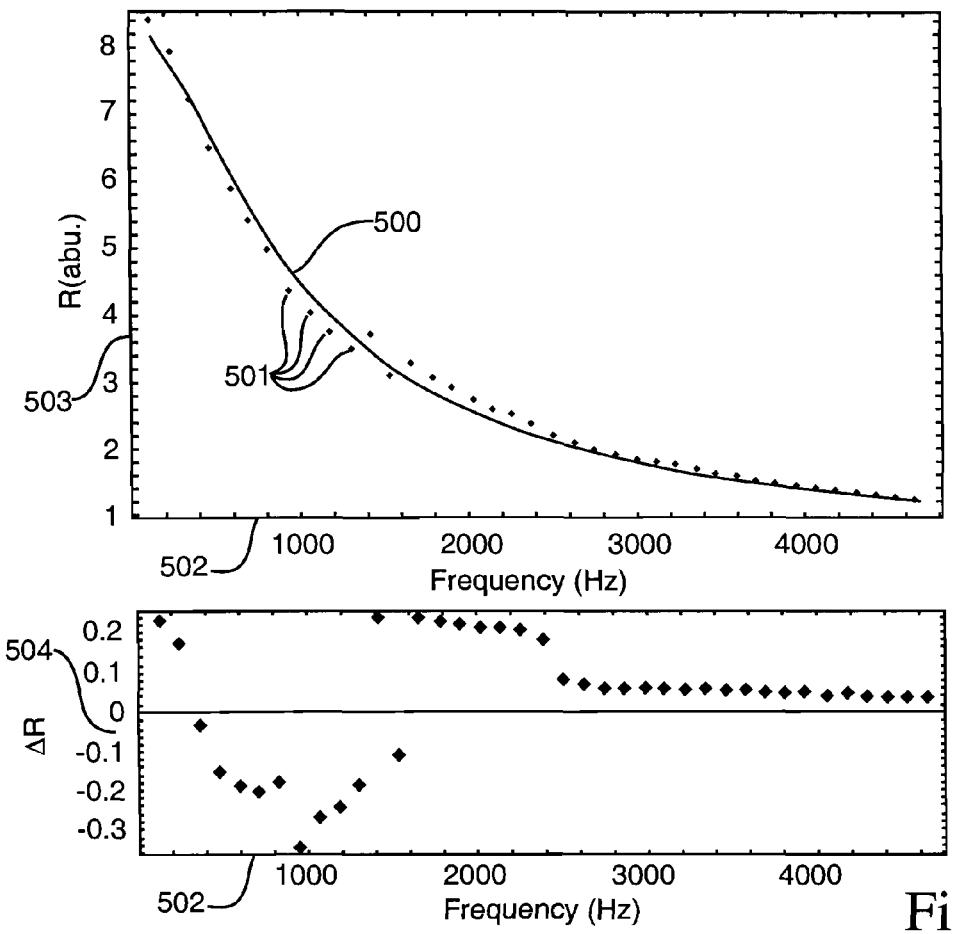
FIG. 5 is a graph of a Vaseline glass emission at various drive frequencies and curve fit.
Figure 6:
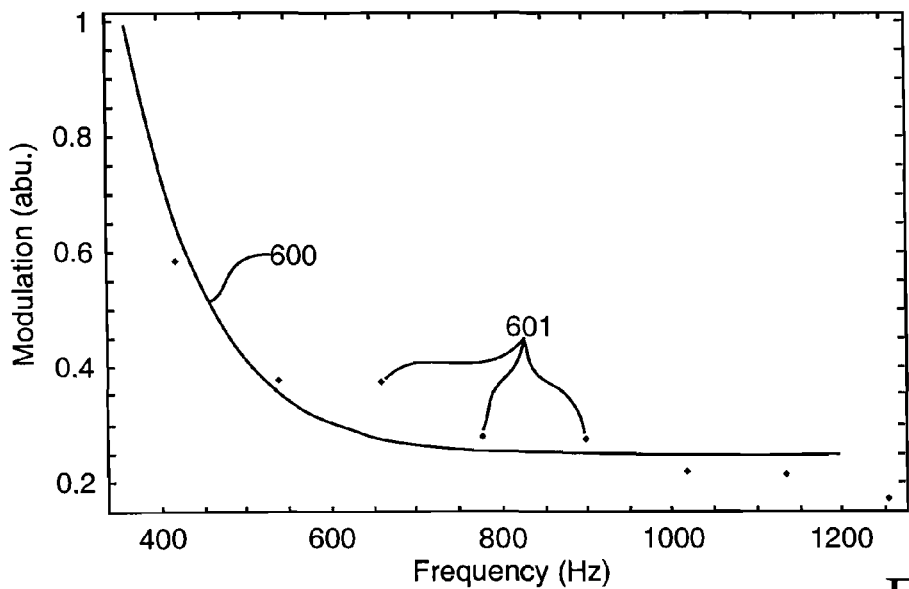
FIG. 6 is a graph of exponential curve fit to lamp modulation frequency.
Figure 7:
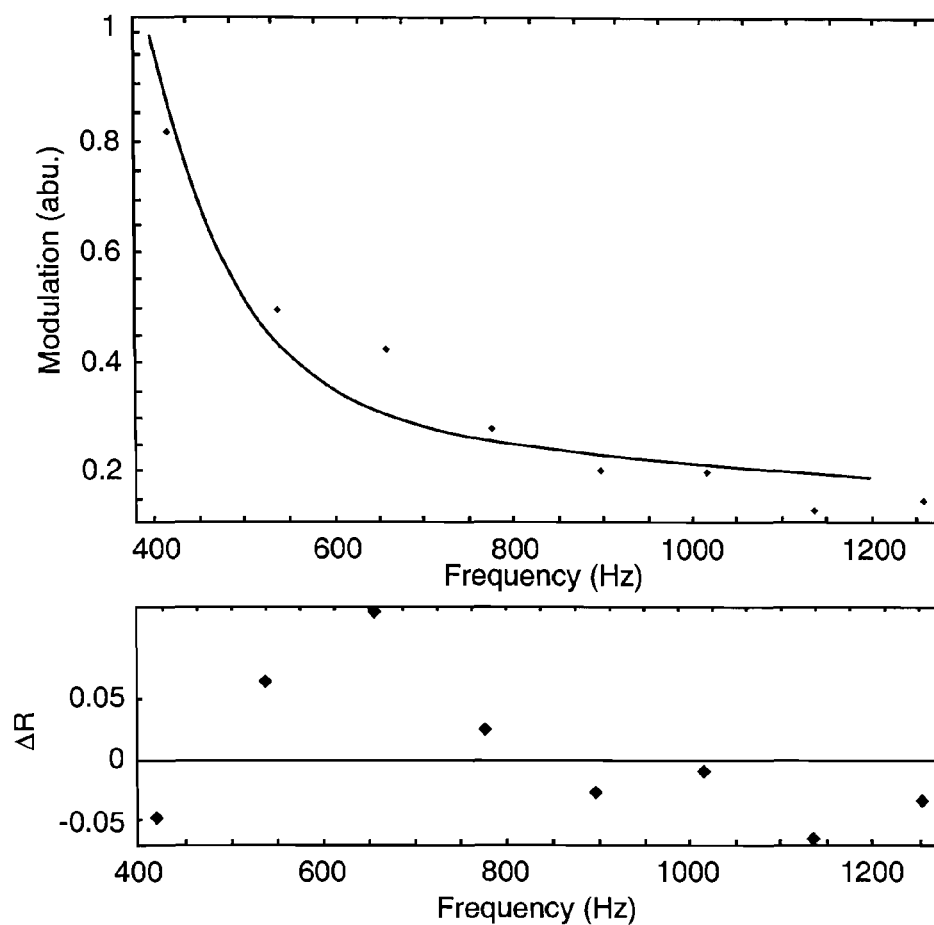
FIG. 7 is a graph showing modulation of the Vaseline glass sample with a mercury vapor lamp.

FIG. 5 shows a graph of Vaseline glass emission at various drive frequencies and curve fit using an LED as the excitation source. In FIG. 5, the x-axis 502 represents the modulation frequency and the y-axis 503 represents modulation amplitude. As predicted by theory, the modulation amplitude decreases with increasing modulation frequency according to Equation 12. The line 500 in FIG. 5 is a least-squares fit to the data 501 presented in FIG. 5 using Equation 12. Ideally the plot of the residuals, the second rectangular graph of FIG. 5, (AR) would appear equally scattered about zero. The nature of the residuals indicates more complicated physics than the simple, single exponential decay modeled by the fit. FIG. 6 is a plot of the lamp modulation without a sample. FIG. 6 is the excitation amplitude, which will be used to normalize the raw fluorescence data. FIG. 7 is a plot of the modulation of the Vaseline glass after it has been normalized using the data in FIG. 6. FIG. 7 is a graph showing modulation of the Vaseline glass sample with a mercury vapor lamp. It should be noted that FIG. 7 represents what could be expected from a remote detection collection, whereas FIG. 5 represents laboratory conditions where the modulation frequency is controlled via a function generator. The bottom graph of FIG. 7 shows the error in the fit to the data where the scatter of the residuals indicates that the simple exponential fit provides an adequate first order fit.

The second uranyl containing sample used in operation and to prove the concept of the preferred arrangement of the invention was yellow cake, which is $U_3O_8$ and is actually a mixture of $UO_2$ and $UO_3$ oxides. A thin layer of $U_3O_8$ was sealed between two mylar sheets. The mylar was measured to have 80% transmission between 400 and 550 nm. The same three measurements were made using the samples of Vaseline glass and yellow cake; namely, a pulsed temporal measurement, frequency domain fluorimetry using an LED and frequency domain fluorimetry using a mercury vapor lamp. The first two experiments, frequency domain fluorimetry and time based exponential decay using the LED as the excitation source, were used again to establish a baseline lifetime of the sample. The frequency domain fluorimetry measurement yielded a lifetime of 324 μs, while the time based exponential fit yielded 351 μs. Although these two lifetimes have a slightly larger deviation than the Vaseline glass, they establish a lifetime window to gauge the accuracy of the mercury vapor lamp excitation lifetimes according to the present invention.

Lifetimes calculated during the curve fitting of the mercury lamp data, 371 μs, correspond well with the previously described time-based exponential fit and the frequency domain fluorimetry using the LED. Using the data set which includes the background wavelengths from the lamp yields a lifetime of 366 μs.

In the FIG. 3 preferred arrangement of the invention, a lock-in amplifier is used to detect the fluorescence at the modulation frequency in order to separate the response of the fluorophore at each of the individual modulation frequencies. The excitation frequency response function is determined by moving the monochromator wavelength to 396 nm and recording the amplitude from the lock-in amplifier as a function generator frequency is scanned from 1-4000 Hz. In the traditional frequency domain technique, the LED was modulated with a sinusoidal signal in order to avoid multi-frequency excitation. The monochromator wavelength is then repositioned to 530 nm, the peak of the fluorescence, and the magnitude of the fluorescence is measured as a function of frequency from the lock-in amplifier.

The real utility of the present invention requires an examination of the geometrical configuration of the source and detector to determine if a usable and reliable signal can be captured at realistic operational distances. There are many unknowns, such as real world concentrations of $UO_2^{2+}$ and atmospheric conditions at observation time. The following describes a conservative approximation of the signal at the detector.

The fundamental equation for radiometry is, $$L_s = \frac{\partial^2 \Phi_s}{\partial A_s \cos\theta_s \partial \Omega_d} \qquad \text{Eq (10)}$$

where $L_s$ is the radiance of the source in $$\frac{watt}{m^2 Sr},$$

$\Phi_s$ is the flux of the source in watts, $A_s$ is the area of the source in $m^2$, $\theta_s$ is the angle between the source-detector ray and the source surface normal ($\cos\theta_s$ provides projected area of the source), and $\Omega_d$ is the solid angle subtended by the detector defined as $$\Omega_d = \frac{A_d \cos\theta_d}{R^2}$$

where $A_d$ is the area of the detector, $\theta_d$ is the angle between the source-detector ray and the detector surface normal, ($\cos\theta_d$ provides projected area of the detecting surface) and R is the source-to-detector range. The irradiance on a detecting surface in $$\frac{watt}{m^2},$$

is then $$E_d = \int \frac{L_s \cos\theta_s \cos\theta_d}{R^2} dA_s. \quad \text{Eq (11)}$$

In a preferred arrangement of the invention, the irradiance on the ground due to the lamp is estimated by assuming the lamp is emitting as a point source of uniform intensity into the lower hemisphere and has a reflector collecting the radiation in the upper hemisphere and distributing it uniformly downward into a 60° cone. It is known in the art that a bulb with a reflector radiates power within a cone of half angle of 60°. The ground irradiance is $$E_{ground}(r,h) = \frac{\Phi_{lamp}}{2\pi} \left[ \frac{\cos\theta_d(r,h)}{2(r^2+h^2)} + \frac{1}{h^2 \cos 60°} \right], \quad \text{Eq (12)}$$

where r is the radial distance out from the center point directly below the lamp, h is the height of the lamp and $\Phi_{lamp}$ is the total lamp power.

Although the ground is often approximated as Lambertian (i.e., scatters equally in all directions), we include the more realistic case of increased reflectance as incident angles approach grazing incidence. The assumption of a purely Lambertian surface would increase fluorophore emission and decrease lamp reflection as incident angle $\theta_d$ increases. Ground reflectance was parameterized using the Schlick approximation for Fresnel reflectance as $$\rho(r,h)=\rho_{diff}+(1-\rho_{diff})[1-\cos\theta_d(r,h)]^5 \quad \text{Eq (13)}$$

where hemispherical reflectances near normal incidence for common construction materials such as concrete and asphalt can range from $0.1 < \rho_{diff} < 0.35$ in the blue/UV and are consistently ~0.05 higher in the green.

By integrating the lamp's spectrum over the wavelengths of interest (see FIG. 1), it can be seen that 50% of the total output is in the blue/UV region ($\eta_{exc}$=0.5) and approximately 0.5% is in the green region ($\eta_{refl}$=0.005). While we included an increase in reflectance as incident angles approach grazing, which is normally associated with more specular reflection, we are assuming that the reflected light is perfectly diffused by the ground, because this provides a much simpler mathematical model than performing a full bi-directional reflectance distribution function radiosity computation. Realistically, specular reflection does not remain perfect but is scattered into a specular lobe—we have merely broadened this lobe to its full extent. This approach should provide the most conservative estimate, since more light is scattered in the direction of the observer from the entire illuminated area than would be if these rays were to be reflected only into their specular direction. With this, the radiances of the reflected lamp in the green and the fluorophore are $$L_{refl}(r,h) = \frac{[\rho(r,h)+0.05]\eta_{refl}E_{ground}(r,h)}{\pi} \quad \text{Eq (14)}$$

$$L_{fluor}(r,h) = \frac{[1-\rho(r,h)]\eta_{exc}\eta_{QE}\eta_{ppm}E_{ground}(r,h)}{\pi} \quad \text{Eq (15)}$$

respectively, where $0.5 < \eta_{QE} < 0.8$ is the quantum efficiency of the fluorophore and $\eta_{ppm}$ accounts for the concentrations of the uranium compounds in the ground. While naturally occurring concentrations are <50 ppb in vegetation and 1-10 ppm in soil [10], it is expected that accidental releases would yield higher concentrations, and since concrete is highly porous, complete contamination removal would be difficult. The flux collected by a detecting surface in watts is $$\Phi_d = \int \int \frac{L_s \cos\theta_s \cos\theta_d}{r^2} dA_s dA_d.$$

The fluxes of the reflected lamp in the green and the fluorophore at a collection optic are $$\Phi_{refl}(h) = \frac{\pi^2 D_{opt}^2 \cos\theta_{obs}}{2R_{obs}^2} \int_0^{r_{max}} rL_{refl}(r,h)dr \quad \text{Eq (16)}$$

$$\Phi_{fluor}(h) = \frac{\pi^2 D_{opt}^2 \cos\theta_{obs}}{2R_{obs}^2} \int_0^{r_{max}} rL_{fluor}(r,h)dr \quad \text{Eq (17)}$$

respectively, where $D_{opt}$ is the diameter of the optic aperture, $\theta_{obs}$ is the observation angle measured from the surface normal, $R_{obs}$ is the source-to-observer range, and $$r_{max} = \frac{D_{det}R_{obs}}{2f/\#D_{opt}}$$

is the maximum radial distance over which the flux is integrated, assuming the field of view is centered on the point directly below the lamp, where $D_{det}$ is the detector size and f/# is of the optical system.

A commonly used photodiode is employed in this example that has a flat response over the frequencies of interest (120-1500 Hz). Although detectors are available with a higher spectral response, it is this detector's extremely low noise equivalent power (NEP) of $$2 - \frac{femtowatt}{\sqrt{Hz}}$$

that makes it attractive for this application. Using a noise-equivalent bandwidth, $\Delta f$=0.05 Hz, from the line-width of US power, integration time is $$\tau_{int} = \frac{1}{2\Delta f} = 10 \text{ s}$$

and NEP≅=1 femtowatt. The photodiode also has size, $D_{det}$=3 mm. As a conservative example, for a 400-watt lamp at a height of 9.1 m, $\rho_{do}$=0.35, fluorophore concentration of 10 ppm and quantum efficiency of 50%, an observation distance of 10 km at $\theta_{obs}$=30°, and an f/2 optical system with a 10-inch optic, the collected fluorophore flux is >1 picowatt. This three order-of-magnitude margin above the NEP should account for losses not included here, like atmospheric extinction and turbulence, and a signal-to-noise ratio desired to be much greater than one.

Although not required, the scenario where the fractional contribution, $f_B$, of the lamp's reflected signal is less than half the total signal may be desirable for unambiguous extraction of the fluorophore lifetime. This is a more taxing scenario, but also achievable.

Here, $f_B$ is independent of lamp flux and $\theta_{obs}$ because $f_B$ is a ratio. For a lamp height of 9.1 m, $\rho_{diff}$=0.35, fluorophore quantum efficiency of 50%, and an f/2 optical system with 3-mm detector, observation of a fluorophore concentration of 2% meets this requirement with a 2-inch optic at a range of 1 km, a 4-inch optic at 5 km or an 7.5-inch optic at 10 km. FIG. 8b shows that for a lamp height of 9.1 m, fluorophore quantum efficiency of 50%, observation distance of 10 km, and an f/2 optical system with a 10-inch optic and 3-mm detector, although observation of a fluorophore concentration of 0.1% never meets this requirement, observation of a fluorophore concentration of 1% meets this requirement for $\rho_{diff}$<0.2 and of a 2% concentration for $0.1 \leq \rho_{diff} \leq 0.35$.

The use of simultaneous multiple frequency excitation may also enhance detection by allowing parallel, multichannel data collection, reducing loiter time over the target area or increasing data collection time. For frequency domain fluorimetry with laser induced fluorescence, the pulsing of the laser is accomplished by stepping through the frequencies and allowing integration time at each step in order to reduce noise. With the present invention, the data is collected at each frequency simultaneously, allowing noise reducing integration time to be increased for all frequencies.

The described arrangement has been demonstrated in a laboratory setting using single-pixel photodetectors; however, this apparatus could also be deployed with a fast framing camera, which has the advantage of providing an image of the fluorophore's location.

The arrangement of the present invention demonstrates a remote detection system and method using a multi-frequency excitation of a common mercury vapor lamp. Although this technique is not as precise as conventional laser techniques, it does offer greater power at much reduced price—our mercury lamp cost less than $25.00 at a home improvement store. The disclosed invention also has additional broader application in active remote sensing, such as chemical/biological agent detection through the use of tagants, which act as the fluorophore identifying the chemical/biological agent.

While the apparatus and method herein described constitute a preferred embodiment of the invention, it is to be understood that the invention is not limited to this precise form of apparatus or method and that changes may be made therein without departing from the scope of the invention, which is defined in the appended claims.

What is claimed is:

1. An efficient and portable method for remote detection of a target material through frequency domain fluorimetry comprising the steps of:
   choosing a target material to detect and identify;
   selecting a mercury vapor lamp, coupled to a power line carrying a power frequency and higher harmonics thereof, said mercury vapor lamp in close proximity to said target material for use as a target material fluorophore excitation source;
   sensing sinusoidal modulation of said mercury vapor lamp resulting from said power frequency and higher harmonics from a distance of at least one kilometer;
   detecting fluorescence from said target material through excitation from said mercury vapor lamp;
   measuring an amplitude and a phase angle of said sensed sinusoidal modulation;
   measuring an amplitude and a phase angle of said detected fluorescence;
   comparing said amplitude and phase angle of said sensed sinusoidal modulation with said amplitude and phase angle of said fluorescence; and
   determining a lifetime of said target material and a corresponding identity of said target material.

2. The method of claim 1 wherein said determining step further comprises remotely determining identity of said a target material.

3. The method of claim 2 wherein said selecting step further comprises selecting a mercury vapor lamp to illuminate a target material facility parking lot.

4. The method of claim 2 wherein said selecting step further comprises selecting a mercury vapor lamp affixed to a target material facility.

5. The method of claim 1 wherein said determining step further comprises remotely a taggant associated with a chemical agent of interest.

6. The method of claim 1 wherein said determining step further comprises remotely identifying a taggant associated with a biological agent of interest.

7. The method of claim 1 further comprising the step of filtering said sinusoidal modulation from said sensing step.

8. The method of claim 1 further comprising the step of filtering said fluorescence from said detecting step.

9. The method of claim 1 wherein said sensing step further comprises sensing sinusoidal modulation of said mercury vapor lamp from said selecting step using a photodetector.

10. The method of claim 1 wherein said measuring step further comprises measuring said sinusoidal modulation of said mercury vapor lamp amplitude and a phase angle from said sensing step and comparing the difference to said fluorescence from said material amplitude and phase angle from said detecting step using a lock-in amplifier.

11. The method of claim 1 wherein said determining step further comprises determining lifetime of said target material and corresponding identity of said target material by the process of curve fitting.

12. An efficient and portable method for remote detection of a target material through frequency domain fluorimetry comprising the steps of:
   choosing a target material to remotely identify and detect;
   selecting a mercury vapor lamp affixed to a target material facility for use as a target material fluorophore excitation source;
   sensing and filtering, using a photodetector, sinusoidal modulation of said mercury vapor lamp due to power line fluctuations from said selecting step;
   detecting and filtering fluorescence from said target material through excitation from said mercury vapor lamp from a distance of at least one kilometer;
   measuring an amplitude and a phase angle of said sensed and filtered sinusoidal modulations;
   measuring an amplitude and a phase angle of said detected and filtered fluorescence;
   comparing, using a lock-in amplifier, said amplitude and phase angle of said sensed and filtered sinusoidal modulation with said amplitude and said phase angle of detected and filtered fluorescence; and
   determining a lifetime of said target material and a corresponding identity of said target material by the process of curve fitting.

13. An efficient and portable remote detection system of frequency domain fluorimetry for target material identification of a target material using a mercury vapor lamp for use as a target material fluorophore excitation source comprising:
- sensing means for sensing sinusoidal modulation of the mercury vapor lamp, the mercury vapor lamp at a distance of at least one kilometer from the sensing means, the sensing means lacking any electrical or physical connection with the mercury vapor lamp;
- detecting means for detecting fluorescence from the target material through excitation from said the mercury vapor lamp to determine a target material amplitude and phase angle;
- a lock-in amplifier for measuring sinusoidal modulation amplitude and phase angle of the mercury vapor lamp and means for comparing the difference to said fluorescence from the target material amplitude and phase angle; and
- curve fitting means for determining lifetime of the target material and corresponding identity of the target material.

14. The device of claim 13 wherein the target material further comprises a target mineral material.

15. The device of claim 13 wherein the target material further comprises a target taggant material associated with a chemical agent of interest.

16. The device of claim 13 wherein the target material further comprises a target taggant material associated with a biological agent of interest.

17. The device of claim 13 wherein the mercury vapor lamp further comprises a mercury vapor lamp to illuminate a target material facility parking lot.

18. The device of claim 13 wherein the mercury vapor lamp further comprises a mercury vapor lamp free affixed to a target material facility.

19. The method of claim 13 further comprising the step of filtering said sinusoidal modulation from said sensing step.

20. The device of claim 13 wherein said sensing means further comprises sensing means and filtering means for sensing and filtering sinusoidal modulation of the mercury vapor lamp.

21. The device of claim 13 wherein said sensing means further comprises a silicon detector for sensing and sinusoidal modulation of the mercury vapor lamp.

22. An efficient and portable method for remote detection of a target material through frequency domain fluorimetry with a fluorophore detection system comprising the steps of:
- choosing a target material to detect and identify;
- selecting a preexisting mercury vapor lamp in fixed close proximity to said target material for use as a target material fluorophore excitation source, said preexisting mercury vapor lamp decoupled from said detection system;
- remotely sensing sinusoidal modulation of said preexisting mercury vapor lamp from said selecting step due to power line fluctuations;
- remotely detecting fluorescence from said target material through excitation from said preexisting mercury vapor lamp;
- measuring an amplitude and a phase angle of said sensed sinusoidal modulation
- measuring an amplitude and a phase angle of said detected fluorescence;
- comparing said amplitude and phase angle of said sensed sinusoidal modulation with said amplitude and said phase angle of said fluorescence; and
- determining lifetime of said target material and corresponding identity of said target material.

* * * * *